(12) United States Patent
Ishihara et al.

(10) Patent No.: US 8,916,206 B2
(45) Date of Patent: Dec. 23, 2014

(54) NANOPARTICLES CONTAINING WATER-SOLUBLE NON-PEPTIDE LOW-MOLECULAR WEIGHT DRUG

(75) Inventors: Tsutomu Ishihara, Ohta-ku (JP); Yutaka Mizushima, Minato-ku (JP); Ayako Mizushima, legal representative, Minato-ku (JP)

(73) Assignee: LTT Bio-Pharma Co., Ltd., Tokyo (JP)

( * ) Notice: Subject to any disclaimer, the term of this patent is extended or adjusted under 35 U.S.C. 154(b) by 1481 days.

(21) Appl. No.: 12/159,023

(22) PCT Filed: Nov. 29, 2006

(86) PCT No.: PCT/JP2006/323820
§ 371 (c)(1),
(2), (4) Date: Feb. 9, 2009

(87) PCT Pub. No.: WO2007/074604
PCT Pub. Date: Jul. 5, 2007

(65) Prior Publication Data
US 2009/0317479 A1    Dec. 24, 2009

(30) Foreign Application Priority Data
Dec. 26, 2005   (JP) ................. 2005-372001

(51) Int. Cl.
*A61K 9/50*   (2006.01)
(Continued)

(52) U.S. Cl.
CPC .............. *A61K 9/5153* (2013.01); *A61K 9/0019* (2013.01); *A61K 9/0024* (2013.01);
(Continued)

(58) Field of Classification Search
CPC ... A61K 31/5575; A61K 33/24; A61K 33/26; A61K 33/30; A61K 33/32; A61K 33/34; A61K 9/0019; A61K 9/1647; A61K 31/557; A61K 31/57; A61K 45/06; A61K 47/34; A61K 47/38
USPC ............ 424/501; 514/573, 179; 977/773, 788
See application file for complete search history.

(56) References Cited

U.S. PATENT DOCUMENTS

| | | | |
|---|---|---|---|
| 2,938,916 A | 5/1960 | Christensen et al. | |
| 3,746,728 A | 7/1973 | Gordon et al. | |

(Continued)

FOREIGN PATENT DOCUMENTS

| | | |
|---|---|---|
| AU | 695323 B2 | 8/1998 |
| EP | 0092918 A2 | 11/1983 |

(Continued)

OTHER PUBLICATIONS

Verrecchia et al., Journal of Controlled Release, 36, 1995, 49-61.*

(Continued)

*Primary Examiner* — Aradhana Sasan
(74) *Attorney, Agent, or Firm* — Drinker Biddle & Reath LLP (57) ABSTRACT

Drug-containing nanoparticles are provided that enable effective targeting and sustained-release of a water-soluble, non-peptide, low-molecular weight drug and cause reduced accumulation of the drug in the liver. The nanoparticles containing a water-soluble, non-peptide, low-molecular weight drug are obtained by hydrophobicizing the water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer. The nanoparticles have favorable targeting and sustained-release properties and cause reduced accumulation of the drug in the liver.

14 Claims, 1 Drawing Sheet

(51) Int. Cl.
| | |
|---|---|
| *A61K 31/19* | (2006.01) |
| *A61K 31/56* | (2006.01) |
| *A61K 9/51* | (2006.01) |
| *A61K 9/00* | (2006.01) |
| *A61K 9/19* | (2006.01) |
| *A61K 31/5575* | (2006.01) |
| *A61K 33/24* | (2006.01) |
| *A61K 33/26* | (2006.01) |
| *A61K 33/30* | (2006.01) |
| *A61K 33/32* | (2006.01) |
| *A61K 33/34* | (2006.01) |
| *A61K 45/06* | (2006.01) |
| *A61K 47/34* | (2006.01) |
| *A61K 47/38* | (2006.01) |

(52) U.S. Cl.
CPC ............... *A61K 9/19* (2013.01); *A61K 9/5192* (2013.01); *A61K 31/5575* (2013.01); *A61K 31/56* (2013.01); *A61K 33/24* (2013.01); *A61K 33/26* (2013.01); *A61K 33/30* (2013.01); *A61K 33/32* (2013.01); *A61K 33/34* (2013.01); *A61K 45/06* (2013.01); *A61K 47/34* (2013.01); *A61K 47/38* (2013.01)
USPC ........................... 424/501; 514/573; 514/179

(56) References Cited

U.S. PATENT DOCUMENTS

| | | | |
|---|---|---|---|
| 4,129,650 A | 12/1978 | Betzing et al. | |
| 4,652,441 A | 3/1987 | Okada et al. | |
| 5,271,945 A | 12/1993 | Yoshioka et al. | |
| 5,690,957 A | 11/1997 | Nishiura et al. | |
| 5,698,590 A | 12/1997 | Nishiura et al. | |
| 5,989,463 A | 11/1999 | Tracy et al. | |
| 6,143,211 A | 11/2000 | Mathiowitz et al. | |
| 6,372,730 B1 | 4/2002 | deLong et al. | |
| 2001/0038854 A1* | 11/2001 | Hata et al. ................ | 424/468 |
| 2003/0228366 A1* | 12/2003 | Shih et al. ................ | 424/486 |
| 2005/0214377 A1 | 9/2005 | Mistry et al. | |
| 2006/0088598 A1 | 4/2006 | Mizushima et al. | |
| 2006/0233883 A1 | 10/2006 | Ishihara et al. | |
| 2008/0226704 A1 | 9/2008 | Kigoshi et al. | |
| 2009/0317479 A1 | 12/2009 | Ishihara et al. | |
| 2010/0129456 A1* | 5/2010 | Ishihara et al. ........... | 424/489 |
| 2011/0262548 A1 | 10/2011 | Mizushima et al. | |

FOREIGN PATENT DOCUMENTS

| | | | | |
|---|---|---|---|---|
| EP | 1002529 | A1 | 5/2000 | |
| EP | 1398025 | A1 | 3/2004 | |
| JP | 532457 | | 1/1978 | |
| JP | 58-191714 | A | 11/1983 | |
| JP | 2-78629 | A | 3/1990 | |
| JP | 8-217691 | A | 8/1996 | |
| JP | 9-110828 | A | 4/1997 | |
| JP | 9-124593 | A | 5/1997 | |
| JP | 9-151136 | A | 6/1997 | |
| JP | 9-157368 | A | 6/1997 | |
| JP | 09-208494 | A | 8/1997 | |
| JP | 10-072375 | A | 3/1998 | |
| JP | 2849608 | | 1/1999 | |
| JP | 11-279184 | A | 10/1999 | |
| JP | 2003506454 | A | 2/2003 | |
| JP | 2003-520210 | A | 7/2003 | |
| JP | 2003520210 | A | 7/2003 | |
| JP | 2006-248992 | A | 9/2006 | |
| WO | WO-96/20698 | A2 | 7/1996 | |
| WO | WO-99/09992 | A1 | 3/1999 | |
| WO | WO-03/101493 | A1 | 12/2003 | |
| WO | WO 2004/084871 | A1 * | 10/2004 | ............... A61K 9/51 |
| WO | WO 2005/089926 | A1 | 9/2005 | |
| WO | WO-2007074604 | A1 | 7/2007 | |

OTHER PUBLICATIONS

T. Verrecchia et al., "Non-stealth (poly(lactic acid/albumin)) and stealth (poly(lactic acid-polyethylene glycol)) nanoparticles as injectable drug carriers," Journal of Controlled Release, vol. 36, 1995, pp. 49-61.

J. Matsumoto et al., "Preparation of nanoparticles consisted of poly(L-lactide)-poly(ethylene glycol)-poly(L-lactide) and their evaluation in vitro," International Journal of Pharmaceuticals, vol. 185, 1999, pp. 93-101.

E. Allemann et al., "PEG-coated poly(lactic acid) nanoparticles for the delivery of hexadecafluoro zinc phthalocyanine to EMT-6 mouse mammary tumours," Journal of Pharm. Pharmacol., vol. 47, No. 5, 1995, pp. 382-387.

International Search Report mailed Mar. 6, 2007, in PCT/2006/323820.

International Search Report mailed Mar. 6, 2007 in PCT International Application No. PCT/2006/323820, filed Nov. 29, 2006.

International Search Report mailed May 13, 2008 in PCT Application No. PCT/JP2008/157167 filed Apr. 11, 2008.

International Preliminary Report on Patentability dated Jul. 1, 2008 in PCT International Application No. PCT/JP2006/323820, filed Nov. 29, 2006.

International Preliminary Report on Patentability dated Nov. 24, 2009 in PCT International Application No. PCT/JP2008/057167, filed Apr. 11, 2008.

Wikipedia page For Surfactant, available at http://en.wikipedia.org/wiki/Surfactant, Jul. 6, 2011.

Wikipedia page for PEG, available at http://en.wikipedia.org/wiki/Polyethylene_glycol, Jul. 6, 2011.

Huh et al., "Drug Delivery Technology," vol. 3, No. 5, Jul./Aug. 2003.

Horisawa, "Prolonged Anti-Inflammatory Action of DL-Lactide-Glycolide Copolymer Nanospheres Containing Betamethasone Sodium Phosphate for an Intra-Articular Delivery System in Antigen-Induced Rabbit," Pharmaceutical Research, 2002, 19(4), 403-410.

Stahl et al., "Handbook of Pharmaceutical Salts: Properties, Selection, and Use," 2002, Publisher: Wiley-Vch, Weinheim.

International Search Report mailed Jun. 14, 2004 in PCT International Application No. PCT/JP2004/003246, filed Mar. 11, 2004.

International Preliminary Report on Patentability issued Oct. 1, 2005 in PCT International Application No. PCT/JP2004/003246, filed Mar. 11, 2004.

International Search Report issued Nov. 24, 2009 in PCT International Application No. PCT/JP2009/067885.

International Preliminary Report on Patentability issued Jun. 21, 2011 in PCT International Application No. PCT/JP2009/067885.

Takeda et al., "Synthesis of Prostaglandin $E_1$ Phosphate Derivatives and Their Encapsulation in Biodegradable Nanoparticles," Pharmaceutical Research 2009, vol. 26, No. 7, pp. 1792-1800.

Shizuka et al., "Synthesis of Isoprostanyl Phosphatidylcholine and Isoprostanyl Phosphatidylethanolamine," Journal of Organic Chemistry, 2006, vol. 71, No. 4, pp. 1330-1334.

* cited by examiner

NANOPARTICLES CONTAINING WATER-SOLUBLE NON-PEPTIDE LOW-MOLECULAR WEIGHT DRUG

CROSS REFERENCE TO RELATED APPLICATIONS

This application is a National Stage of International Application No. PCT/JP2006/323820 filed Nov. 29, 2006, and which claims benefit of Japanese Patent Application No. 2005-372001 filed Dec. 26, 2005, which are incorporated herein in their entirety.

TECHNICAL FIELD

The present invention relates to drug-containing nanoparticles, and in particular, to nanoparticles that contain a water-soluble, non-peptide, low-molecular weight drug. The nanoparticles of the present invention have favorable targeting and sustained-release properties, cause reduced accumulation of the drug in the liver, and have an improved long-circulating property.

BACKGROUND ART

A number of studies have been conducted in an attempt to encapsulate drugs in microparticles and nanoparticles of poly(lactic-co-glycolic acid) (which may be referred to as "PLGA," hereinafter) or poly(lactic acid) (which may be referred to as "PLA," hereinafter).

For example, U.S. Pat. No. 4,652,441 (Patent Document 1) describes PLGA microcapsules containing physiologically active polypeptides, and a production method thereof. Published Japanese Translation of a PCT Application No. Hei 10-511957 (Patent Document 2) describes PLGA nanoparticles for intravascular administration containing various drugs. Also, Japanese Laid-Open Patent Publication No. Hei 8-217691 (Patent Document 3) discloses a sustained-release formulation including PLGA microcapsules encapsulating water-insoluble or hardly water-soluble polyvalent metal salts of physiologically active, water-soluble peptide compounds.

However, none of the prior art patents mentions the concept of hydrophobicizing a water-soluble, non-peptide, low-molecular weight drug by a metal ion, and encapsulating the hydrophobicized drug in a PLA-PEG block copolymer or a PLGA-PEG block copolymer in which PLA or PLGA is bound to polyethylene glycol (which may be referred to as "PEG," hereinafter).

International Patent Publication No. WO 2003/101493 (Patent Document 4) filed by the present applicant describes a preparation including drug-encapsulating PLGA or PLA fine particles that have a surfactant adhered to the surface thereof. International Patent Publication No. WO 2004/84871 (Patent Document 5) also filed by the present applicant describes a preparation including PLGA or PLA nanoparticles encapsulating a water-soluble, non-peptide, low-molecular weight pharmaceutical agent hydrophobicized by a metal ion and having a surfactant adsorbed on the surface thereof.

However, the fine particles disclosed in Patent Document 4 can encapsulate only low amounts of the drug. The particles also tend to burst at an early stage of administration and cannot therefore achieve ideal sustained-release performance. The nanoparticles disclosed in Patent Document 5 tend to accumulate in the liver when intravenously administered despite their improved encapsulation rate of drug and decreased early burst.

Block copolymers composed of poly(lactic acid) or poly(lactic-co-glycolic acid) and polyethylene glycol are described in different publications. For example, Japanese Laid-Open Patent Publication No. Sho 58-191714 (Patent Document 6) describes a block copolymer composed of polyethylene glycol, a hydrophilic polymer, and poly(lactic acid), a hydrophobic polymer. Japanese Laid-Open Patent Publication No. Hei 9-157368 (Patent Document 7) describes a purification method of a triblock copolymer including poly(lactic acid)-polyethylene glycol-poly(lactic acid).

One proposed application of block copolymers composed of poly(lactic acid) or poly(lactic-co-glycolic acid) and polyethylene glycol is in pharmaceutical compositions. For example, Japanese Patent Publication Laid-Open No. Hei 2-78629 (Patent Document 8) describes a pharmaceutical composition including a copolymer of a copolymer of lactic acid and/or glycolic acid and polyethylene glycol, with a polypeptide added thereto. Japanese Laid-Open Patent Publication No. Hei 9-151136 (Patent Document 9) describes a solution containing a protein along with a poly(lactic acid)-polyethylene glycol copolymer.

However, nanoparticles are not known that are obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer.

Neither are drug-containing nanoparticles known that are obtained by hydrophobicizing a water-soluble, non-peptide, low-molecular weight drug by a metal ion, and encapsulating the hydrophobicized drug in nanoparticles of a poly(lactic acid)-polyethylene glycol block copolymer or a poly(lactic-co-glycolic acid)-polyethylene glycol block copolymer, and that have favorable targeting and sustained-release properties, cause reduced accumulation of the drug in the liver, and have an improved long-circulating property.

Patent Document 1 U.S. Pat. No. 4,652,441
Patent Document 2 Published Japanese Translation of a PCT Application No. Hei 10-511957
Patent Document 3 Japanese Laid-Open Patent Publication No. Hei 8-217691
Patent Document 4 International Patent Publication No. WO 2003/101493
Patent Document 5 International Patent Publication No. WO 2004/84871
Patent Document 6 Japanese Laid-Open Patent Publication No. Sho 58-191714
Patent Document 7 Japanese Laid-Open Patent Publication No. Hei 9-157368
Patent Document 8 Japanese Laid-Open Patent Publication No. Hei 2-78629
Patent Document 9 Japanese Laid-Open Patent Publication No. Hei 9-151136

DISCLOSURE OF THE INVENTION

Problems to be Solved by the Invention

In view of the above-described circumstances, it is an object of the present invention to provide nanoparticles that contain a water-soluble, non-peptide, low-molecular weight drug and that can effectively target the water-soluble, non-peptide, low-molecular weight drug to the target site, achieve ideal sustained-release of the drug, and cause reduced side effects by causing reduced accumulation of the drug in the liver.

In the course of studies to achieve the aforementioned object, the present inventors have found that particular drug-containing nanoparticles obtained in a particular manner have favorable targeting and sustained-release properties, cause reduced accumulation of the drug in the liver, and have an improved long-circulating property. Specifically, the nanoparticles are obtained by hydrophobicizing a water-soluble, non-peptide, low-molecular weight drug by a metal ion, and encapsulating the hydrophobicized drug in nanoparticles of a poly(lactic acid)-polyethylene glycol block copolymer or a poly(lactic-co-glycolic acid)-polyethylene glycol block copolymer. It is this finding that led to the present invention.

Means for Solving the Problems

Accordingly, the present invention provides nanoparticles that contain a water-soluble, non-peptide, low-molecular weight drug and that have favorable targeting and sustained-release properties, cause reduced side effects by causing reduced accumulation of the drug in the liver, and have an improved long-circulating property.

The present invention also provides intravenous preparations, local injection preparations, nasal preparations, ophthalmic preparations, inhalation preparations, spray preparations and other parenteral preparations that contain the nanoparticles as an active ingredient.

More specifically, the present invention comprises the following:

(1) A nanoparticle containing a water-soluble, non-peptide, low-molecular weight drug, the nanoparticle obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer;

(2) A nanoparticle containing a water-soluble, non-peptide, low-molecular weight drug, the nanoparticle obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer, and a poly(lactic acid) or a poly(lactic-co-glycolic acid) copolymer;

(3) The nanoparticle containing a water-soluble, non-peptide, low-molecular weight drug according to 1 or 2 above, further containing a basic low-molecular weight compound mixed therewith;

(4) The nanoparticle containing a water-soluble, non-peptide, low-molecular weight drug according to 1, 2 or 3 above, further containing a surfactant;

(5) The nanoparticle containing a water-soluble, non-peptide, low-molecular weight drug according to any of 1 to 4 above, wherein the nanoparticle has a diameter in the range of 20 to 300 nm, and preferably in the range of 50 to 200 nm;

(6) The nanoparticle containing a water-soluble, non-peptide, low-molecular weight drug according to 1, 2 or 3 above, wherein the metal ion is one or two or more of zinc ion, iron ion, copper ion, nickel ion, beryllium ion, manganese ion or cobalt ion;

(7) The nanoparticle containing a water-soluble, non-peptide, low-molecular weight drug according to 1, 2 or 3 above, wherein the water-soluble, non-peptide, low-molecular weight drug includes a phosphate group, a sulfate group or a carboxyl group for hydrophobicizing by the metal ion;

(8) The nanoparticle containing a water-soluble, non-peptide, low-molecular weight drug according to 1, 2, 3 or 7 above, wherein the water-soluble, non-peptide, low-molecular weight drug is an anti-inflammatory steroid, a nonsteroidal anti-inflammatory drug, prostaglandin or a derivative thereof, an anti-microbial drug or an anticancer drug;

(9) The nanoparticle containing a water-soluble, non-peptide, low-molecular weight drug according to 1, 2 or 3 above, wherein the poly(lactic acid)-polyethylene glycol block copolymer or the poly(lactic-co-glycolic acid)-polyethylene glycol block copolymer has a weight average molecular weight in the range of 3,000 to 20,000;

(10) The nanoparticle containing a water-soluble, non-peptide, low-molecular weight drug according to 3 above, wherein the basic low-molecular weight compound is one or two or more selected from (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenetylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine and trimethylenediamine;

(11) The nanoparticle containing a water-soluble, non-peptide, low-molecular weight drug according to 4 above, wherein the surfactant is one or two or more selected from phosphatidylcholine, polyoxyethylene (20) sorbitan monooleate, polyoxyethylene (20) sorbitan monolaurate, polyoxyethylene (20) sorbitan monostearate, polyoxyethylene (20) sorbitan monopalmitate, polyoxyethylene (20) sorbitan trioleate, polyoxyethylene (80) octylphenyl ether, polyoxyethylene (20) cholesterol ester, lipid-polyethylene glycol, polyoxyethylene hydrogenated castor oil, and fatty acid-polyethylene glycol copolymer;

(12) A parenteral preparation containing as an active ingredient the nanoparticle containing a water-soluble, non-peptide, low-molecular weight drug according to 1 to 11;

(13) The parenteral preparation according to 12 above, wherein the preparation is an intravenous preparation, a local injection preparation, a nasal preparation, an ophthalmic preparation, an inhalation preparation or a spray preparation;

(14) A method for producing the nanoparticle containing a water-soluble, non-peptide, low-molecular weight drug according to 1 above, the method including the steps of:

mixing a water-soluble, non-peptide, low-molecular weight drug with a metal ion in a solvent to produce a hydrophobicized drug; and mixing with the resulting mixture a poly(lactic acid)-polyethylene glycol block copolymer or a poly(lactic-co-glycolic acid)-polyethylene glycol block copolymer;

(15) A method for producing the nanoparticle containing a water-soluble, non-peptide, low-molecular weight drug according to 2 above, the method including the steps of:

mixing a water-soluble, non-peptide, low-molecular weight drug with a metal ion in a solvent to produce a hydrophobicized drug; and mixing with the resulting mixture a poly(lactic acid)-polyethylene glycol block copolymer or a poly(lactic-co-glycolic acid)-polyethylene glycol block copolymer, and a poly(lactic acid) or a poly(lactic-co-glycolic acid) copolymer;

(16) The method for producing the nanoparticle containing a water-soluble, non-peptide, low-molecular weight drug according to 14 or 15 above, further including the step of mixing a basic low-molecular weight compound; and (17) The method for producing the nanoparticle containing a water-soluble, non-peptide, low-molecular weight drug according to 16 above, wherein the basic low-molecular weight compound is one or two or more selected from (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenetylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine and trimethylenediamine.

Thus, the nanoparticle of the present invention containing a water-soluble, non-peptide, low-molecular weight drug is obtained by hydrophobicizing a water-soluble, non-peptide, low-molecular weight drug with a metal ion, and reacting the hydrophobicized drug with a poly(lactic acid)-polyethylene glycol block copolymer or a poly(lactic-co-glycolic acid)-polyethylene glycol block copolymer to encapsulate the drug in the nanoparticle.

Effect of the Invention

The nanoparticles containing a water-soluble, non-peptide, low-molecular weight drug provided in accordance with the present invention have improved targeting of the water-soluble, non-peptide, low-molecular weight drug and sustained-release properties, cause reduced side effects by causing reduced accumulation of the drug in the liver, and have an improved long-circulating property.

Thus, the nanoparticles of the present invention facilitate the targeting and sustained release of water-soluble, non-peptide, low-molecular weight drugs, a technical task that has not been effectively fulfilled by conventional techniques. The nanoparticles of the present invention also reduce the side effects caused by the accumulation of these drugs in the liver, and improve the blood levels of the drugs.

BEST MODE FOR CARRYING OUT THE INVENTION

In one embodiment of the present invention, the nanoparticles containing a water-soluble, non-peptide, low-molecular weight drug can be obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer. A surfactant may be added to stabilize the resulting nanoparticles.

In another embodiment of the present invention, the nanoparticles containing a water-soluble, non-peptide, low-molecular weight drug can be obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer, and a poly(lactic acid) or a poly(lactic-co-glycolic acid) copolymer.

A surfactant may also be added to the above-described nanoparticles containing a water-soluble, non-peptide, low-molecular weight drug to stabilize the resulting nanoparticles and prevent aggregation of the particles.

The nanoparticles containing a water-soluble, non-peptide, low-molecular weight drug provided by such the way described above can be administered in the form of a parenteral preparation, such as an intravenous preparation, a local injection preparation, a nasal preparation, an ophthalmic preparation, an inhalation preparation and a spray preparation.

According to the present invention, the nanoparticles containing a water-soluble, non-peptide, low-molecular weight drug can be produced in the following manner.

A water-soluble, non-peptide, low-molecular weight drug is mixed with a metal ion in an organic solvent or an aqueous organic solvent to hydrophobicize the drug. To this mixture, a poly(lactic acid)-polyethylene glycol block copolymer or a poly(lactic-co-glycolic acid)-polyethylene glycol block copolymer is added and the mixture is stirred. The resulting mixture is then dispersed in water to form the desired nanoparticles.

Alternatively, a solution obtained by dissolving the poly(lactic acid)-polyethylene glycol block copolymer or the poly(lactic-co-glycolic acid)-polyethylene glycol block copolymer in the solvent, an aqueous solution of the water-soluble, non-peptide, low-molecular weight drug, and an aqueous solution of the metal ion may be simultaneously added and mixed together to form the nanoparticles.

The metal ion may be any of zinc ion, iron ion, copper ion, nickel ion, beryllium ion, manganese ion and cobalt ion. One or two or more of these ions are used in the form of water-soluble metal salts. Of these ions, zinc ion and iron ion are preferably used in the form of zinc chloride and iron chloride, respectively.

The solvent used in the above-described reaction is preferably an organic solvent, such as acetone, acetonitrile, ethanol, methanol, propanol, dimethylformamide, dimethylsulfoxide and dioxane, or an aqueous solvent thereof. Of these solvents, acetone and dimethylformamide are particularly preferred.

The water-soluble, non-peptide, low-molecular weight drug preferably includes a phosphate group, a sulfate group or a carboxyl group that binds to the metal ion to facilitate the hydrophobicization of the drug. Also, the drug preferably has a molecular weight of 1,000 or less.

While a variety of water-soluble, non-peptide, low-molecular weight drugs may be used in the present invention, water-soluble anti-inflammatory steroids, nonsteroidal anti-inflammatory drugs, prostaglandin or derivatives thereof, anti-microbial drugs or anticancer drugs are preferably used. Specific examples of these drugs include, but are not limited to, anti-inflammatory steroids, such as betamethasone phosphate, dexamethasone phosphate, prednisolone phosphate, hydrocortisone phosphate, prednisolone succinate and hydrocortisone succinate; nonsteroidal anti-inflammatory drugs, such as loxoprofen sodium, ibuprofen, ketoprofen, diclofenac and fenbufen; prostaglandin $E_1$, prostaglandin $E_2$ and derivatives thereof; antimicrobial drugs, such as vancomycin, chloramphenicol succinate, latamoxef, cefpirome, clindamycin phosphate and carumonam; and anticancer drugs, such as vincristine and vinblastine.

The poly(lactic acid)-polyethylene glycol block copolymer (PLA-PEG) or the poly(lactic-co-glycolic acid)-polyethylene glycol block copolymer (PLGA-PEG) can be produced by reacting PLA or PLGA (referred to as "block A") with PEG (referred to as "block B") in the presence of a condensation agent such as ethylene dimethylaminopropyl carbodiimide. However, similar commercially available block copolymers may also be used.

To achieve the object of the present invention, the block copolymer may be any of the following types: A-B, A-B-A and B-A-B. These block copolymers preferably have a weight average molecular weight of 3,000 to 20,000.

In addition to the poly(lactic acid)-polyethylene glycol block copolymer or the poly(lactic-co-glycolic acid)-polyethylene glycol block copolymer, a poly(lactic acid) or a poly(lactic-co-glycolic acid) copolymer may further be added to the nanoparticles of the present invention containing a water-soluble, non-peptide, low-molecular weight drug. Increasing the ratio of the poly(lactic acid) or the poly(lactic-co-glycolic acid) copolymer is likely to lead to an increased nanoparticle size and a decreased amount of the drug encapsulated by the nanoparticles.

In such a case, a basic low-molecular weight compound may be added to increase the encapsulation rate, or the amount of the drug encapsulated by the nanoparticles, up to about 10%.

Examples of such basic low-molecular weight compounds include (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenetylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine and trimethylenediamine. Of these compounds, secondary and tertiary amines are preferred with diethanolamine being particularly preferred.

A surfactant may then be added to the resulting nanoparticles containing a water-soluble, non-peptide, low-molecular weight drug to stabilize the nanoparticles and prevent aggregation of the particles. This makes the nanoparticles suitable in making preparations containing the nanoparticles.

Examples of the surfactant that can be used include phosphatidylcholine, polyoxyethylene (20) sorbitan monooleate, polyoxyethylene (20) sorbitan monolaurate, polyoxyethylene (20) sorbitan monostearate, polyoxyethylene (20) sorbitan monopalmitate, polyoxyethylene (20) sorbitan trioleate, polyoxyethylene (80) octylphenyl ether, polyoxyethylene (20) cholesterol ester, lipid-polyethylene glycol, polyoxyethylene hydrogenated castor oil, and fatty acid-polyethylene glycol copolymer. One or two or more selected from these surfactants are preferably used.

The nanoparticles containing a water-soluble, non-peptide, low-molecular weight drug provided in accordance with the present invention has a particle size in the range of 20 to 300 nm, and preferably in the range of 50 to 200 nm. The particle size can be determined depending on the type of the target site targeted by a particular drug.

For example, when the drug is intended to treat diseases such as arthritis, cancer and arteriosclerosis obliterans, the nanoparticles having a particle size of 50 to 200 nm are preferably injected intravenously. The particle size can be adjusted by varying the amount of the solvent to dissolve the PLA-PEG or PLGA-PEG block copolymer, the solvent being preferably acetone. Increasing the amount of acetone leads to a decreased particle size of the nanoparticles. Also, the nanoparticles having a larger particle size can encapsulate a larger amount of the drug.

The nanoparticles of the present invention containing a water-soluble, non-peptide, low-molecular weight drug prepared in the above-described manner are separated from the solution or the suspension containing the nanoparticles by a proper purification technique, such as centrifugation, ultrafiltration, gel filtration, filtration by filter and fiber dialysis. The separated nanoparticles are freeze-dried and stored.

A stabilizer and/or a disperser is/are preferably added to the separated nanoparticles so that the freeze-dried preparation can be resuspended prior to administration. Examples of such stabilizers and dispersers include sucrose, trehalose and carboxymethylcellulose sodium.

The nanoparticles containing a water-soluble, non-peptide, low-molecular weight drug provided in accordance with the present invention can be used in various pharmaceutical products provided in the form of parenteral preparations such as intravenous preparations, local injection preparations, nasal preparations, ophthalmic preparations, inhalation preparations and spray preparations. The features and advantages of the nanoparticles of the present invention can be most effectively exploited when they are prepared as an intravenous preparation.

Pharmaceutically acceptable bases and other additives are also used in preparing the above-described parenteral preparations. Specific examples of the base and the additive include physiological saline; sugars, such as monosaccharides, disaccharides, sugar alcohols and polysaccharides; polymer additives, such as hydroxyethylcellulose, hydroxypropylcellulose and methylcellulose; and ionic or nonionic surfactants. These bases and the additives are properly selected depending of the dosage form.

EXAMPLES

The present invention will now be described with reference to examples, which are not intended to limit the scope of the invention in any way.

Example 1

Synthesis of PLA-PEG Block Copolymer

One gram of PLA (Mn 4900, Wako Pure Chemical Industries Ltd.), 0.831 g of terminal amino-modified PEG (Mp 2000, NOF Corp.), 266 mg of a condensation agent (ethyldimethylaminopropylcarbodiimide hydrochloride, or EDC), and 152 mg of dimethylaminopyridine were dissolved in 20 mL of dimethylformamide (DMF). The solution was stirred at room temperature for 16 hours. Subsequently, the reaction mixture was subjected to dialysis against water at 4° C. for 16 hours (MWCO 10000, SpectraPor7, Funakoshi Corp.), followed by ultrafiltration (YM-50, MWCO 50000, Amicon). The filtrate was freeze-dried to obtain a PLA-PEG block copolymer. The PLA-PEG block copolymer was qualitatively analyzed by gel filtration chromatography (GPC). Using a different PLA (Mn 3600, Wako Pure Chemical Industries Ltd.) and a different terminal amino-modified PEG (Mp 5000, NOF Corp.) at the same molar ratio as the above reaction, a reaction was carried out in the same manner as the above reaction.

The peak observed in the GPC chart of the reaction product was shifted to the high-molecular-weight side relative to the peaks observed in the GPC charts of PLA or PEG alone or a mixture of PLA and PEG, indicating that the product was a PLA-PEG block copolymer. The GPC chart of the reaction product did not show the peak corresponding to PEG, indicating that unreacted PEG was removed by purification.

A PLGA-PEG block copolymer was also synthesized by carrying out a similar reaction in which PLA was replaced by PLGA (Mn 4900, Wako Pure Chemical Industries Ltd.).

Example 2

Production of PLA-PEG Block Copolymer Nanoparticles Encapsulating a Steroid

One hundred milligrams of a PLA-PEG block copolymer or 100 mg of a mixture of the PLA-PEG block copolymer and PLA were dissolved in 2 to 6 mL acetone. To this solution, 27 μL (375 mg/mL) of an aqueous solution of betamethasone phosphate was added, immediately followed by 133 μL of a 1M aqueous zinc chloride solution. The mixture was allowed to stand at room temperature for 30 minutes. Using a pipette, the mixture was then added to 40 mL water under stirring. This caused the formation of nanoparticles. To the resulting nanoparticle suspension, 1 mL of a 0.5 M aqueous sodium citrate solution and 100 μL (200 mg/mL) of an aqueous solution of Tween 80 (polyoxyethylene (20) sorbitan monooleate) were added. Subsequently, the nanoparticles were purified from the suspension by ultrafiltration (YM-50, MWCO 50000, Amicon), followed by gel filtration (PD-10, Amersham), followed by filtration through a filter (1.2 μm).

The addition of Tween 80 prior to purification does not change the particle size of the nanoparticles during the purification. However, the nanoparticles aggregated in the absence of Tween 80.

The particle size of the resulting nanoparticles was measured by a dynamic light scattering particle size analyzer and the amount of betamethasone phosphate encapsulated by the nanoparticles (encapsulation rate) was determined by HPLC.

As it turned out, the encapsulation rate, or the amount of betamethasone phosphate encapsulated by the nanoparticles, was 1 to 6%. The encapsulation rate, or the amount of betamethasone phosphate encapsulated by the nanoparticles of the PLA-PEG block copolymer, increased as the particle size increased. The encapsulation rate of betamethasone phosphate decreased as the mixing ratio of PLA was increased relative to the PLA-PEG block copolymer.

The relationship between the amount of acetone used and the particle size was shown in Table 1. The relationship between the mixing ratio of PLA and the particle size is shown in Table 2.

TABLE 1

Relationship between the amount of acetone used and the particle size of the nanoparticle

| Amount of acetone used (mL) | 2 | 3 | 4 | 5 |
|---|---|---|---|---|
| Particle size Dw (nm) | 128 | 106 | 91 | 87 |

TABLE 2

Effect of the mixing ratio of PLA to PLA-PEG block copolymer on the particle size of the nanoparticle

| | PLA-PEG:PLA (ratio by weight) | | | | |
|---|---|---|---|---|---|
| | 100:0 | 70:30 | 60:40 | 30:70 | 10:90 |
| Particle size Dw (nm) | 91 | 112 | 134 | 168 | 187 |

As can be seen from the results of Table 1, increasing the amount of acetone to dissolve 100 mg of the PLA-PEG block copolymer resulted in the formation of smaller nanoparticles. As can be seen from the results of Table 2, increasing the mixing ratio of PLA to the PLA-PEG block copolymer resulted in the formation of larger nanoparticles.

Example 3

Cellular Uptake of Nanoparticles

Ten milligrams of rhodamine, a fluorescent dye, was dissolved in a solution of 100 mg of a PLA-PEG block copolymer in acetone. As in Example 2, nanoparticles encapsulating rhodamine were prepared and purified.

Macrophage-like RAW cells (mouse leukemic monocytes) were inoculated at $10 \times 10^4$ cells/well and were cultured overnight in a MEM medium containing 10% fetal bovine serum. Subsequently, the nanoparticles encapsulating rhodamine prepared above were added to the medium and the cell culture was incubated for 2 hours at 37° C. The cells were washed with PBS, fixed in 4% formaldehyde and observed with a fluorescent microscope.

Figure 1:
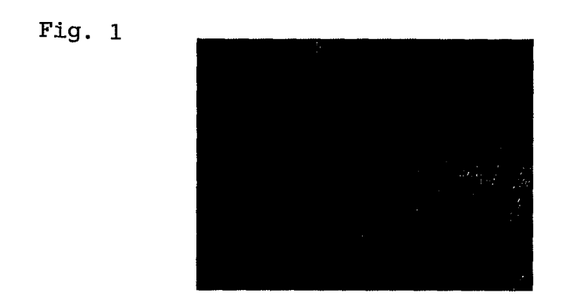
FIG. 1 is a fluorescent micrograph to show cellular uptake of nanoparticles encapsulating rhodamine. The micrograph shows only cells with no nanoparticles added thereto.
Figure 2:
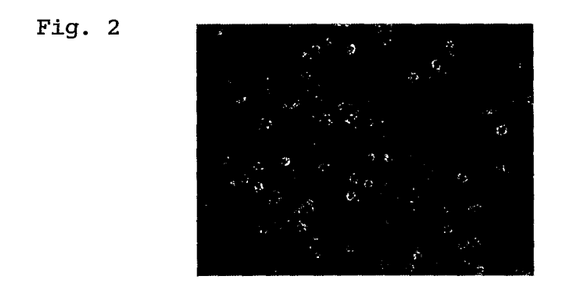
FIG. 2 is a fluorescent micrograph to show cellular uptake of nanoparticles encapsulating rhodamine. The micrograph shows cells to which the nanoparticles described in Example 2 of International Patent Publication No. WO 2004/84871 have been added.
Figure 3:
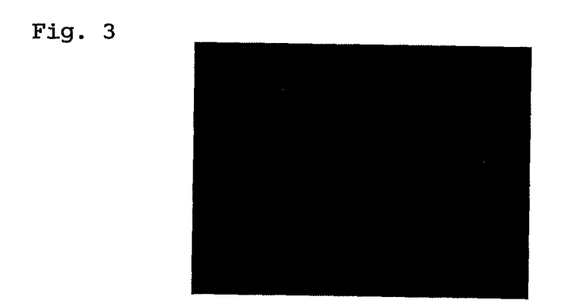
FIG. 3 is a fluorescent micrograph to show cellular uptake of nanoparticles encapsulating rhodamine. The micrograph shows cells to which the nanoparticles of the present invention have been added.

The results are shown in FIGS. 1 through 3. FIG. 1 is a fluorescent micrograph of nanoparticle-free cells. FIG. 2 is a fluorescent micrograph of cells to which the nanoparticles described in Example 2 of International Patent Publication No. WO 2004/84871 have been added. FIG. 3 is a fluorescent micrograph of cells to which the nanoparticles of the present invention have been added.

As can be seen from FIGS. 1 through 3, the nanoparticles prepared using PLA (nanoparticles described in Example 2 of International Patent Publication No. WO 2004/84871) were significantly taken up by the cells, whereas the nanoparticles prepared using the PLA-PEG block copolymer were hardly taken up by the cells. It has thus been demonstrated that the nanoparticles of the present invention using the PLA-PEG block copolymer show reduced uptake by macrophages.

Example 4

Change in the Accumulation and Retention of Betamethasone Phosphate in the Inflammation Site in Adjuvant Arthritis Rats Fifty microliters of an incomplete Freund's adjuvant solution (DIFCO) containing 6 mg/mL of M. Butyricum Dessicated (DIFCO) was subcutaneously injected into the left hind paw of 7-week-old Lewis rats, weighing 130 to 160 g, under anesthesia with ether. The animals were divided into groups so that there is no significant difference in the volume of the left hind leg between the groups. 10 to 14 days after administration of M. Butyricum, each group was intravenously administered a single dose of the nanoparticles encapsulating betamethasone phosphate (equivalent to 50 μg betamethasone). As a control, another group was intravenously administered a single dose of the PLA nanoparticles encapsulating betamethasone phosphate (nanoparticles described in Example 2 of International Patent Publication No. WO2004/84871).

After a predetermined period of time, the liver and the inflamed leg were excised and homogenized and betamethasone was quantified by immunoassay. Similarly, the blood concentration of betamethasone was determined by immunoassay.

The results are shown in Tables 3 to 5.

TABLE 3

Changes in the concentration of betamethasone per unit weight of liver (ng/mg)

| Elapsed time after administration | 30 min | 1 day | 4 days |
|---|---|---|---|
| Nanoparticles of WO2004/84871 | 6.00 | 2.60 | 1.80 |
| Nanoparticles 1 of the present invention | ND | 1.07 | 0.14 |
| Nanoparticles 2 of the present invention | ND | 1.89 | 0.18 |

ND: Not determined.

Nanoparticles 1 of the present invention: Nanoparticles sized 148 nm and prepared using a 7:3 mixture of PLA (Mn 3600)-PEG (Mp 5000) and PLA (Mn 3600).

Nanoparticles 2 of the present invention: Nanoparticles sized 79 nm and prepared using PLA (Mn 4900)-PEG (Mp 5000).

TABLE 4

Changes in the concentration of betamethasone per unit weight of inflamed leg (ng/mg)

| Elapsed time after administration | 30 min | 1 day | 4 days |
|---|---|---|---|
| Nanoparticles of WO2004/84871 | 0.04 | 0.03 | 0.003 |
| Nanoparticles 1 of the present invention | ND | 1.13 | 0.33 |
| Nanoparticles 2 of the present invention | ND | 0.87 | 0.22 |

ND: Not determined.

The nanoparticles 1 and 2 of the present invention are the same as those shown in Table 3.

TABLE 5

Changes in the blood concentration of betamethasone (ng/mg)

| Elapsed time after administration | 30 min | 1 day |
|---|---|---|
| Nanoparticles of WO2004/84871 | 0.06 | 0.01 |
| Nanoparticles 3 of the present invention | 5.19 | 0.04 |

Nanoparticles 3 of the present invention: Nanoparticles sized 80 nm and prepared using PLA (Mn 3600)-PEG (Mp 5000).

As demonstrated in Tables 3 through 5, betamethasone accumulated intensely in the liver, but only slightly in the inflamed leg in rats receiving the nanoparticles prepared using PLA (nanoparticles described in Example 2 of International Patent Publication No. WO 2004/84871). In comparison, the accumulation of betamethasone decreased in the liver but increased in the inflamed leg in rats that received the PLA-PEG block copolymer nanoparticles prepared by the method of the present invention, as compared to the rats administered the above nanoparticles.

In rats receiving the PLA-PEG block copolymer nanoparticles of the present invention, significant amounts of betamethasone were remaining in the inflamed leg after 4 days. The analysis of the blood concentration of betamethasone revealed that, after 30 minutes, little betamethasone was remaining in the blood of rats receiving the nanoparticles prepared using PLA alone (nanoparticles described in Example 2 of International Patent Publication No. WO 2004/84871), whereas the blood concentration of betamethasone was very high in rats receiving the PLA-PEG block copolymer nanoparticles prepared by the method of the present invention.

Example 5

Suppression of Adjuvant Arthritis

Fifty microliters of an incomplete Freund's adjuvant solution (DIFCO) containing 6 mg/mL of M. Butyricum Dessicated (DIFCO) was subcutaneously injected into the left hind paw of 7-week-old Lewis rats, weighing 130 to 160 g, under anesthesia with ether. The animals were divided into groups so that there is no significant difference in the volume of the left hind leg between the groups. 14 days after administration of M. Butyricum, one group was intravenously administered a single dose of the nanoparticles of the present invention encapsulating betamethasone phosphate (equivalent to 50 μg betamethasone). As controls, other groups were intravenously administered the same amount of an aqueous betamethasone phosphate solution or the PLA nanoparticles encapsulating betamethasone phosphate (nanoparticles described in Example 2 of International Patent Publication No. WO 2004/84871), each administered in a single dose.

The ability of the nanoparticles to suppress arthritic inflammation was analyzed by the water displacement technique by measuring the volume of the left hind legs before and after the administration of the nanoparticles.

The results are shown in Table 6. Inflammation rate shown in Table 6 was determined with respect to the leg volume of the control group (=100) and calculated by the following equation:

Inflammation rate(%)=(measured leg volume−leg volume without adjuvant)/(initial leg volume−leg volume without adjuvant)×100

TABLE 6

Ability of the nanoparticles to suppress adjuvant arthritis

| | Inflammation rate (%) Time after administration (days) | | | | | |
|---|---|---|---|---|---|---|
| | 1 | 2 | 3 | 4 | 6 | 8 |
| Aqueous solution of betamethasone phosphate | 83 | 80 | 82 | 83 | 84 | 81 |
| Nanoparticles of WO2004/84871 | 75 | 74 | 73 | 73 | 77 | 72 |
| Nanoparticles 3 of the present invention | 69 | 60 | 64 | 63 | 65 | 66 |

Each inflammation rate is the average of 4 rats.

The nanoparticles 3 of the present invention are the same as the nanoparticles 3 shown in Table 5.

As can be seen from Table 6, the PLA nanoparticles (nanoparticles described in Example 2 of International Patent Publication No. WO 2004/84871) exhibited stronger ability to suppress inflammation than the aqueous betamethasone phosphate solution. The PLA-PEG block copolymer nanoparticles prepared by the method of the present invention exhibited even stronger ability to suppress inflammation than the PLA nanoparticles.

Example 6

Synthesis of PLA/PLGA-PEG Block Copolymer

Two grams of PEG (NOF Corp., having a terminal methoxy or OH group, Mw=5250), 2 to 6 g of DL-lactide (Tokyo Chemical Industry Co., Ltd., product obtained by dissolving DL-lactide in ethyl acetate to a concentration of 100 g/L and allowing the compound to recrystallize overnight at −40° C.), and tin octoate (0.5 wt %) were placed in a polymerization vessel and thoroughly mixed together. The vessel was evacuated using a hydraulic pump. Subsequently, the reaction vessel was placed in an oil bath at 125° C. to melt the mixture. Once melted, the mixture was further heated to 160° C. and left for 3 to 5 hours. The mixture was then allowed to cool and was dissolved in 20 mL dichloromethane. The solution was slowly added to a large quantity of ice-cold isopropanol for reprecipitation. The resulting precipitate was suspended in water and the suspension was freeze-dried to give a PLA-PEG block copolymer.

The resulting PLA-PEG block copolymer was analyzed by GPC (gel filtration chromatography, solvent=dimethylformamide (containing 10 mM lithium chloride)) and proton NMR.

The ratios of lactide to PEG used are shown in Table 7, along with the molecular weights of the resulting PLA-PEG block copolymers and the ratios of PLA/PEG (by weight) in the PLA-PEG block copolymers.

The results indicate that the reaction rate was about 60%, and that the molecular weight of the reaction product increased as a function of the ratio of the starting materials.

TABLE 7

Synthesis of PLA-PEG block copolymer by polymerization

| No. | ratio of Lactide/PEG (ratio by weight) | Molecular weight (Mn) of PEG (determined by GPC) | Molecular weight (Mn) of PLA (determined by NMR) | Mw/Mn (determined by GPC) | Ratio of PLA/PEG (by weight) |
|---|---|---|---|---|---|
| 1 | 1 | 5130 | 2854 | 1.19 | 0.55 |
| 2 | 2 | 5130 | 6202 | 1.48 | 1.21 |
| 3 | 3 | 5130 | 9975 | 1.42 | 1.94 |

Mn = number average molecular weight;
Mw = weight average molecular weight.

Using a mixture of glycolide (Purac Biochem) and lactide, a similar reaction was carried out to obtain a PLGA-PEG block copolymer.

Example 7

Production of PLA-PEG Block Copolymer Nanoparticles Encapsulating a Steroid

The PLA-PEG block copolymer synthesized in Example 6 and PLA (Wako Pure Chemical Industries Ltd.) were combined to make a total weight of 50 mg. The weighed compounds were dissolved with 1 mL acetone. To this solution, a solution of 7.5 mg diethanolamine in 500 μL acetone was added, followed by 68 μL of a 1M aqueous zinc chloride solution. The mixture was lightly stirred. 28.6 μL of an aqueous solution of betamethasone sodium phosphate (350 mg/mL) was immediately added. The mixture was thoroughly stirred and then allowed to stand at room temperature for about 30 minutes. To a 50 mL sample vial containing 25 mL water, stirred with a 2 cm stirrer bar, the above-prepared reaction mixture was added dropwise using a 3 mL syringe equipped with a 25 G injection needle (the stirrer operated at 1000 rpm, injection needle=26 G, syringe=3 mL syringe from Nipro, addition rate=48 mL/hr). 1 to 2 minutes after the addition was complete, 500 μL of a 0.5M aqueous sodium citrate solution (pH 7) and 125 μL of an aqueous solution of Tween 80 (200 mg/mL) were added. The resulting solution was concentrated by ultrafiltration (YM-50, Amicon), followed by addition of 20 mL of an aqueous solution of Tween 80 (1 mg/mL), followed by concentration again (This was repeated twice). Subsequently, the mixture was centrifuged at 1000 rpm for 5 minutes to remove agglomerates. The particle size was measured by a dynamic light-scattering (DLS) particle size analyzer and the encapsulation rate, or the amount of betamethasone sodium phosphate (BSP) encapsulated by the nanoparticles, was determined by HPLC.

The BSP encapsulation rate of nanoparticles prepared using varying amounts of diethanolamine is shown in Table 8. The mixing ratio of PLA to the block copolymer and the particle size and the BSP encapsulation rate of nanoparticles prepared by varying the mixing ratio of PLA are shown in Tables 9 and 10.

TABLE 8

BSP encapsulation rate of nanoparticles prepared using varying amounts of diethanolamine

| | Amount of diethanolamine used (mg) | | | | | |
|---|---|---|---|---|---|---|
| | 0 | 1 | 2.5 | 5 | 7.5 | 10 |
| Amount of BSP encapsulated by particles (encapsulation rate) (wt %) | 0.12 | 0.84 | 2.12 | 4.23 | 5.12 | 5.24 |

TABLE 9

Particle size and BSP encapsulation rate of nanoparticles prepared by varying the mixing ratio of PLA to block copolymer(determined using block copolymer No. 1 in Table 7)

| | Proportion of PLA present in the form of PLA-PEG block copolymer with respect to total PLA of PLA-PEG block copolymer and PLA (wt %) | | | | | | |
|---|---|---|---|---|---|---|---|
| | 3 | 6 | 14 | 24 | 37 | 56 | 100 |
| Particle size (nm) | 154 | 131 | 103 | 86 | 59 | 49 | 29 |
| Amount of BSP encapsulated by particles (encapsulation rate) (wt %) | 6.21 | 5.99 | 4.82 | 3.81 | 1.66 | 0.46 | 0.01 |

TABLE 10

Particle size and BSP encapsulation rate of nanoparticles prepared by varying the mixing ratio of PLA to block copolymer (determined using block copolymer No. 2 in Table 7)

| | Proportion of PLA present in the form of PLA-PEG block copolymer with respect to total PLA of PLA-PEG block copolymer and PLA (wt %) | | | | | |
|---|---|---|---|---|---|---|
| | 6 | 13 | 30 | 52 | 81 | 100 |
| Particle size (nm) | 126 | 98 | 75 | 69 | 48 | 35 |
| Amount of BSP encapsulated by particles (encapsulation rate) (wt %) | 6.00 | 5.30 | 2.31 | 0.59 | 0.05 | 0.02 |

The nanoparticles prepared by varying the amount of diethanolamine had a particle size of about 100 to 120 nm. The results of Table 8 indicate that the BSP encapsulation rate was affected by the amount of diethanolamine: the encapsulation rate increased as the amount of diethanolamine was increased.

The results of Tables 9 and 10 indicate that, by increasing the proportion of PLA present in the form of the PLA-PEG block copolymer with respect to the total PLA of the PLA-PEG block copolymer and PLA, the resulting nanoparticles tended to have a decreased particle size and a decreased BSP encapsulation rate.

Example 8

Production of PLA-PEG Block Copolymer Nanoparticles Encapsulating prostaglandin E1 (PGE1)

The PLA-PEG block copolymer synthesized in Example 6 and PLA (Wako Pure Chemical Industries Ltd.) were combined to make a total weight of 25 mg. The weighed compounds were dissolved with 250 μL acetone. To this solution, 250 μL of a solution of prostaglandin E1 (PGE1) in acetone (20 mg/mL) was added, followed by a solution of 7.9 mg diethanolamine in 250 μL acetone. The 25 μL of a 500 mM solution of ferric chloride in acetone was immediately added. The mixture was stirred and then allowed to stand at room temperature for about 10 minutes. To a 50 mL sample vial containing 25 mL water, stirred with a 2 cm stirrer bar, the above-prepared acetone solution was added dropwise using a 3 mL syringe equipped with a 26 G injection needle (the stirrer operated at 1000 rpm, injection needle=26 G, syringe=3 mL syringe from Nipro, addition rate=48 mL/hr). The reaction mixture was allowed to stand in an ice bath for 20 minutes and then centrifuged at 1000 rpm (4° C., 10 min) to remove the precipitate. 2.5 mL of a 500 mM aqueous EDTA solution (pH 7) was added to the supernatant. The resulting solution was concentrated by ultrafiltration (YM-50, Amicon), followed by addition of a 50 mM aqueous EDTA solution (pH 7), followed by concentration again (This was repeated twice). The resulting concentrated suspension was sonicated for 30 seconds and filtered on a gel filtration apparatus (PD-10, Amersham, buffer=0.1% aqueous solution of Tween 80). This was repeated twice. Subsequently, the filtered product was centrifuged at 1000 rpm for 5 minutes to remove agglomerates. The particle size was analyzed by DLS and the amount of PGE1 encapsulated by the nanoparticles was determined by HPLC.

The PGE1 encapsulation rate of nanoparticles prepared using varying amounts of diethanolamine is shown in Table 11.

TABLE 11

PGE1 encapsulation rate of nanoparticles prepared using varying amounts of diethanolamine

| | Amount of diethanolamine used (mg) | | | | |
|---|---|---|---|---|---|
| | 0.0 | 2.6 | 5.2 | 10.5 | 15.7 |
| Amount of PGE1 encapsulated by particles (encapsulation rate) (wt %) | 0.02 | 0.45 | 0.74 | 2.92 | 1.92 |

The nanoparticles prepared by varying the amount of diethanolamine had a particle size of about 100 to 120 nm. The results of Table 11 indicate that the PGE1 encapsulation rate was affected by the amount of diethanolamine: the encapsulation rate increased as the amount of diethanolamine was increased.

Example 9

Suppression of Adjuvant Arthritis

As in Example 5, the ability of nanoparticles to suppress adjuvant arthritis was evaluated. Each inflammation rate is the average of 7 rats. Nanoparticles of the present invention containing betamethasone phosphate equivalent to 40 μg betamethasone were intravenously administered in a single dose.

As a control, another group of rats was intravenously administered the same amount of an aqueous solution of betamethasone phosphate in a single dose.

The nanoparticles 4 of the present invention were prepared by mixing the block copolymer synthesized according to Example 7 and PLA (Mn 26000) at a ratio of 16:84 (by weight).

The ability of the nanoparticles 4 of the present invention to suppress inflammation is shown in Table 12.

TABLE 12

Ability of the nanoparticles to suppress inflammation in adjuvant arthritis rats

| | Inflammation rate (%) Time after administration (days) | | | | | | |
|---|---|---|---|---|---|---|---|
| | 1 | 2 | 3 | 4 | 5 | 7 | 9 |
| Aqueous solution of betamethasone phosphate | 81 | 83 | 83 | 78 | 78 | 79 | 79 |
| Nanoparticles 4 of the present invention | 65 | 64 | 69 | 68 | 72 | 70 | 70 |

Significant difference: $p < 0.05$

The results demonstrate that the nanoparticles of the present invention have stronger ability to suppress inflammation than the aqueous solution of betamethasone phosphate and ensure sustained effect of the drug.

Example 10

Intravenous Injection

The PLA-PEG block copolymer nanoparticles obtained in Example 2 encapsulating betamethasone phosphate were added to an aqueous sucrose solution and the solution was freeze-dried. To the freeze-dried product, 0.5% carmellose or injection water was added from a separate vial to form an intravenous injection.

INDUSTRIAL APPLICABILITY

As set forth, the nanoparticles of the present invention containing a water-soluble, non-peptide, low-molecular weight drug can effectively target the water-soluble, non-peptide, low-molecular weight drug to the target site, achieve ideal sustained-release of the drug, have reduced side effects by causing reduced accumulation of the drug in the liver, and have an improved long-circulating property. Therefore, the nanoparticles of the present invention are useful pharmaceutical products that find a wide range of industrial applications.

The invention claimed is:

1. A nanoparticle containing a water-soluble, non-peptide, low-molecular weight drug, the nanoparticle obtained by hydrophobicizing a water-soluble, non-peptide, low-molecular weight drug by a metal ion, and reacting the hydrophobicized drug with a poly(lactic acid)-polyethylene glycol block copolymer or a poly(lactic-co-glycolic acid)-polyethylene glycol block copolymer, and a poly(lactic acid) or a poly(lactic-co-glycolic acid) copolymer, wherein the poly(lactic acid)-polyethylene glycol block copolymer or the poly(lactic-co-glycolic acid)-polyethylene glycol block copolymer has a weight average molecular weight in a range of 3,000 to 20,000, and further comprising a basic low molecular weight compound mixed therein.

2. The nanoparticle containing a water-soluble, non-peptide, low-molecular weight drug according to claim 1, further comprising a surfactant.

3. The nanoparticle containing a water-soluble, non-peptide, low-molecular weight drug according to claim 1, wherein the nanoparticle has a diameter in a range of 20 to 300 nm.

4. The nanoparticle containing a water-soluble, non-peptide, low-molecular weight drug according to claim 1, wherein the metal ion is one or two or more of zinc ion, iron ion, copper ion, nickel ion, beryllium ion, manganese ion or cobalt ion.

5. The nanoparticle containing a water-soluble, non-peptide, low-molecular weight drug according to claim 1, wherein the water-soluble, non-peptide, low-molecular weight drug includes a phosphate group, a sulfate group or a carboxyl group for hydrophohicizing by the metal ion.

6. The nanoparticle containing a water-soluble, non-peptide, low-molecular weight drug, according to claim 1, wherein the water-soluble, non-peptide, low-molecular weight drug is an anti-inflammatory steroid, a nonsteroidal anti-inflammatory drug, a prostaglandin or a prostaglandin containing compound, an anti-microbial drug; or an anticancer drug.

7. The nanoparticle containing a water-soluble, non-peptide, low-molecular weight drug according to claim 1, wherein the basic low-molecular weight compound is one or two or more selected from the group consisting of (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermidine, hexamethylenediamine, putrescine, cadaverine, phenetylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine, and trimethylenediamine.

8. The nanoparticle containing a water-soluble, non-peptide, low-molecular weight drug according to claim 2, wherein the surfactant is one or two or more selected from the group consisting of phosphatidylcholine, polyoxyethylene (20) sorbitan monooleate, polyoxyethylene (20) sorbitan monolaurate, polyoxyethylene (20) sorbitan monostearate, polyoxyethylene (20) sorbitan monopalmitate, polyoxyethylene (20) sorbitan trioleate, polyoxyethylene (80) octylphenyl ether, polyoxyethylene (20) cholesterol ester, lipid-polyethylene glycol, polyoxyethylene hydrogenated castor oil, and fatty acid-polyethylene glycol copolymer.

9. A parenteral preparation containing as an active ingredient the nanoparticle containing a water-soluble, non-peptide, low-molecular weight drug according to claim 1.

10. The parenteral preparation according to claim 9, wherein the preparation is an intravenous preparation, a local injection preparation, a nasal preparation, an ophthalmic preparation, an inhalation preparation or a spray preparation.

11. A method for producing the nanoparticle containing a water-soluble, non-peptide, low-molecular weight drug according to claim 1, the method comprising the steps of:
mixing a water-soluble, non-peptide, low-molecular weight drug with a metal ion in a solvent to produce a hydrophobicized drug;
mixing with the resulting mixture a poly(lactic acid)-polyethylene glycol block copolymer or a poly(lactic-co-glycolic acid)-polyethylene glycol block copolymer, and a poly(lactic acid) or a poly(lactic-co-glycolic acid) copolymer; and
mixing a basic low-molecular weight compound.

12. The method for producing the nanoparticle containing a water-soluble, non-peptide, low-molecular weight drug according to claim 11, wherein the basic low-molecular weight compound is one or two or more selected from the group consisting of (dimethylamino)pyridine, pyridine, piperidine, pyrimidine, pyrazine, pyridazine, quinoline, quinuclidine, isoquinoline, bis(dimethylamino)naphthalene, naphthylamine, morpholine, amantadine, aniline, spermine, spermi dine, hexamethylenediamine, putrescine, cadaverine, phenetylamine, histamine, diazabicyclooctane, diisopropylethylamine, monoethanolamine, diethanolamine, triethanolamine, ethylamine, diethylamine, triethylamine, methylamine, dimethylamine, trimethylamine, triethylenediamine, diethylenetriamine, ethylenediamine and trimethylenediamine.

13. The nanoparticle containing a water-soluble, non-peptide, low-molecular weight drug according to claim 2, wherein the nanoparticle has a diameter in a range of 20 to 300 nm.

14. The nanoparticle containing a water-soluble, non-peptide, low-molecular weight drug, according to claim 5, wherein the water-soluble, non-peptide, low-molecular weight drug is an anti-inflammatory steroid, a nonsteroidal anti-inflammatory drug, a prostaglandin or a prostaglandin containing compound, an anti-microbial drug; or an anticancer drug.

* * * * *